United States Patent [19]

Banda et al.

[11] Patent Number: 4,503,038

[45] Date of Patent: Mar. 5, 1985

[54] EXTRACELLULAR NONMITOGENIC ANGIOGENESIS FACTOR AND METHOD OF ISOLATION THEREOF FROM WOUND FLUID

[75] Inventors: Michael J. Banda; Zena Werb; David R. Knighton; Thomas K. Hunt, all of San Francisco, Calif.

[73] Assignee: The Regents of the University of California, Berkeley, Calif.

[21] Appl. No.: 469,935

[22] Filed: Feb. 25, 1983

[51] Int. Cl.³ .................... A61K 35/12; A61K 37/02
[52] U.S. Cl. ........................................ 424/95; 514/21
[58] Field of Search ............. 424/95, 177; 260/112 R

[56] References Cited

PUBLICATIONS

Banda, et al. including Oredsson, S., "Purification . . . from Rabbit Wound Fluid", Fed. Proc. 41(3), 1982, 1085.

*Primary Examiner*—Nicky Chan
*Assistant Examiner*—Jacqueline M. Stone
*Attorney, Agent, or Firm*—Flehr, Hohbach, Test, Albritton & Herbert

[57] ABSTRACT

A nonmitogenic angiogenesis factor is isolated from wound fluid by dialysis to include materials in the molecular size range of 2,000 to 14,000, lyophilization, and chromatography. The nonmitogenic angiogenesis factor is identified by activity by corneal implant assay and by cell migration assay. The angiogenesis factor is also characterized by inactivity by mitogenesis assay.

6 Claims, 3 Drawing Figures

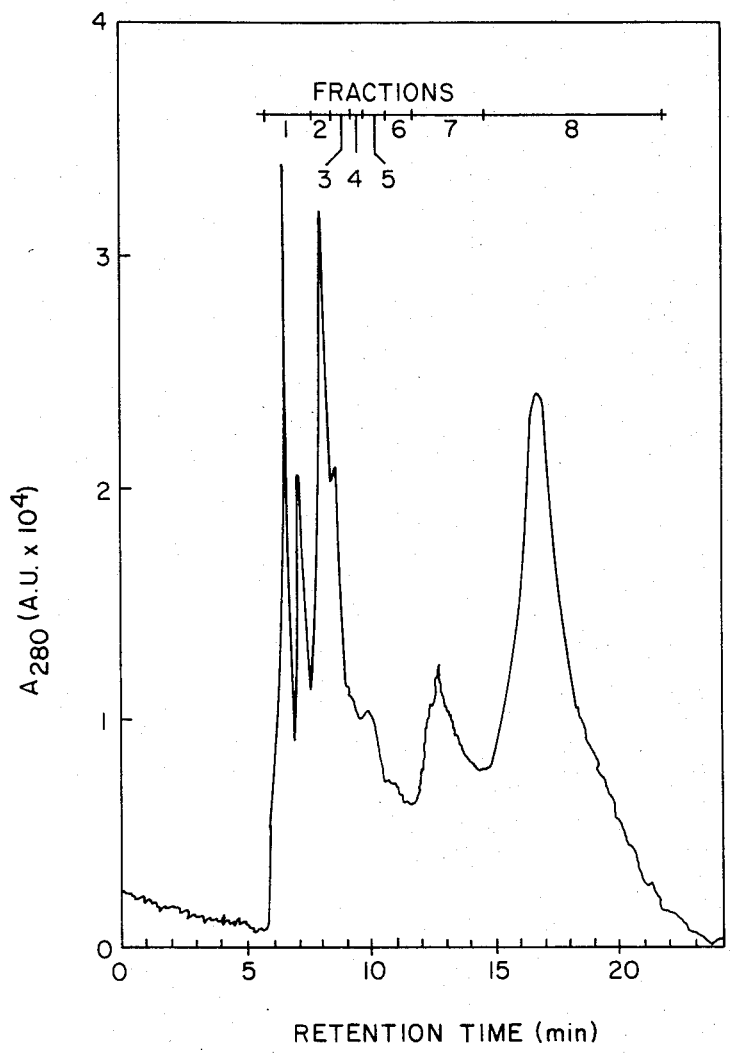
FIG.—1

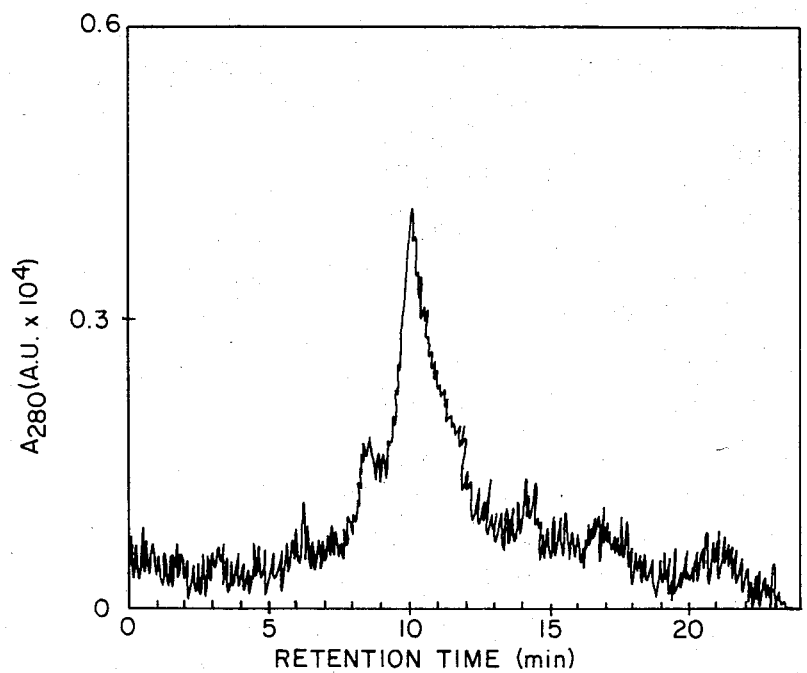
FIG. — 2
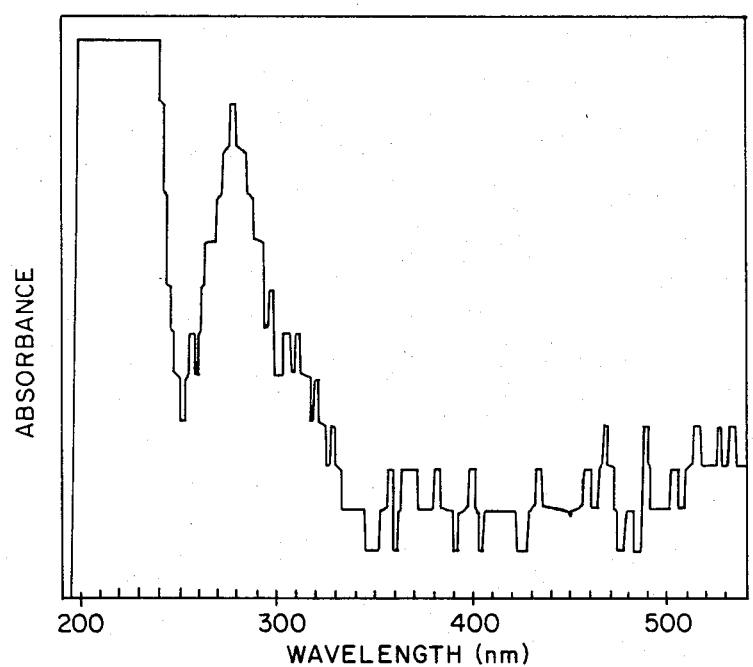
FIG. — 3

EXTRACELLULAR NONMITOGENIC ANGIOGENESIS FACTOR AND METHOD OF ISOLATION THEREOF FROM WOUND FLUID

The government has rights in this invention pursuant to contract number DE-AM03-76-SF01012 from the Department of Energy and Grant number HL26323 and GM27345 from the Department of Health and Human Services.

The present invention is directed to a method of isolating an extracellular nonmitogenic angiogenesis factor from wound fluid and to the product derived therefrom.

Angiogenesis, or new capillary growth, is essential to normal growth and wound healing. It is also an active component of pathologic states such as tumor growth, atherosclerosis, arthritis and diabetic retinopathy. By angiogenesis, the outgrowth of new capillaries is directed toward a specific stimulus. Therefore, the ability to stimulate directed capillary endothelial cell migration is an expected prerequisite of an angiogenesis factor and because this may be stimulated at a distance, the angiogenesis factor must act extracellularly. However, heretofore an extracellular form of an angiogenesis factor has not been isolated.

It is therefore an object of the present invention to provide a method for isolating an extracellular nonmitogenic angiogenesis factor.

It is a further object of the present invention to provide an extracellular nonmitogenic angiogenesis factor.

In the accompanying figures:

FIG. 1 is a HPLC chromatogram of reconstituted lyophilized wound fluid containing nonmitogenic angiogenesis factor.

FIG. 2 is a HPLC chromatogram of purified fraction 5 shown in FIG. 1.

FIG. 3 is a UV spectrum of the purified fraction 5.

It has been unexpectedly found that the angiogenesis factor isolated according to the present invention differs from either Walker 256 carcinoma angiogenesis factor or retinal angiogenesis factor in that the wound fluid angiogenesis factor is not an endothelial cell mitogen. Therefore, it has been discovered that it is not necessary to attribute mitogenic capability to an angiogenic factor that stimulates directed migration of capillary endothelial cells.

The present invention is directed to a product and a method for isolating same from wound fluid comprising the steps of (a) clarifying fluid from the wound of a mammal by centrifugation; (b) dialyzing the clarified fluid from step (a) with acetic acid at about 4° C.; (c) removing insoluble material from the retentate from step (b) by centrifugation; (d) dialyzing the clarified retentate from step (c) with water at about 4° C.; (e) lyophilizing the dialysate from step (d); (f) dissolving the product from step (e) in acetic acid; (g) fractionating the solution from step (f) by size exclusion chromatography; and (h) identifying a fraction from step (g) which exhibits angiogenic activity.

Wound fluid was obtained by pooling fluid withdrawn from stainless steel, wire-mesh wound cylinders implanted 21 days earlier in the flanks of New Zealand White rabbits, according to the method of Schilling et al., (1953) Surg. Gyn. and Obs. 96, 143–149. Each cylinder yielded approximately 10 ml of fluid.

The angiogenic potential of whole untreated wound fluid varied from no detectable activity to as high as 75 units per ml. Serum consistently had no angiogenic activity by the corneal implant assay described below. Acidification of the wound fluid to pH 2.9 by the addition of glacial acetic acid to 0.1N enhanced angiogenic activity 2- to 6-fold and also removed nonangiogenic acid-soluble material. The results are shown below in Table 1.

TABLE 1

| WOUND FLUID AS A SOURCE OF ANGIOGENESIS FACTOR | | |
|---|---|---|
| Source | Units/ml (mean ± SD) | No. of preparations |
| Serum | 0 | 6 |
| Wound fluid | 25 ± 31.6 | 6 |
| Acidified wound fluid | 62 ± 17.7 | 2 |

*Acidified to pH 2.9 with glacial acetic acid; not dialyzed.

Pooled wound fluid was clarified by centrifugation at 20,000×g for 30 minutes at 4° C. The clarified wound fluid was then placed in an $M_r$ 2,000-limit dialysis bag (Spectrapore 6, Spectrum Medical Ind., Los Angeles, CA) and dialyzed against three changes of 10 vol of 0.1N acetic acid at 4° C. Acid-insoluble material was removed from the retentate by centrifugation at 20,000×g for 30 minutes at 4° C.

The retentate contained all of the angiogenic activity and little or no mitogenic activity toward capillary endothelial cells as shown below in Table 2.

TABLE 2

| CAPILLARY ENDOTHELIAL CELL MITOGENESIS | |
|---|---|
| Stage | Mitogenic Index* |
| Wound fluid | 26.90 |
| Acid dialysate | 1.08 |

*[$^3$H]thymidine incorporation, experimental/control = index. Assay volume was 100 μl.

The clarified retentate was then placed in a standard $M_r$ 14,000-limit dialysis bag and dialyzed against 2 liters of 4° C. water. The 2 liters of dialysate were then lyophilized and the retentate was discarded.

The dialyzed and lyophilized wound fluid was reconstituted to 10 mg/ml (wt/vol) (~7 mg protein/ml) in 0.01N acetic acid (Pierce Chem. Co., Rockford, IL). Any insoluble material was removed by filtration through a 0.45 μm0pore-diameter filter (Millipore, Bedford, MA). This material was then applied to a pair of Aquapore OH-100 size-exclusion columns (4.6 mm×250 mm each) fitted with an Aquapore guard cartridge and an Aquapore presaturation column (Brownlee Corp., Santa Clara, CA). Chromatography was carried out with 0.01N acetic acid as the mobile phase delivered at 1.0 ml/min at 25° C. by a Hewlett-Packard model 1084B liquid chromatograph equipped with a model 79825A fraction collector, a model 79842A automatic sampling system, and a model 7987A variable wavelength detector with stop-flow-scan capability. For this column system the theoretical void and total inclusion volumes for globular proteins that do not bind to the column were determined with Blue Dextran ($M_r$ 2×10$^6$, retention time 3.67 min) and K$_3$Fe(CN)$_6$ ($M_r$ 329, retention time 6.11 min).

Angiogenesis was determined by the corneal implant assay according to the method of Gimbrone et al (1974) J. Natl. Cancer Inst. 52, 413–427. The solution to be tested was mixed with an equal volume of Hydron (Hydron Laboratories Inc., New Brunswick, NJ), dropped in 20 μl aliquots onto a polyethylene sheet, then dried under vacuum, according to the method of Langer et al (1976) Nature 263, 797–800. The resulting pellets of polymerized Hydron and test substance were implanted in corneas 2 mm proximal to the superior limbus. Eyes were evaluated from 3 through 14 days after implantation. The sustained growth of well-defined individual capillaries from the limbus toward or into the implant was considered positive for angiogenesis. Angiogenic response was scored blindly on a 0 to 4 relative scale. A normal or negative eye was scored as 0, whereas a maximal response was scored as 4. Because a reading of 4 was maximal it was not used in quantification. A response of 2 on the relative scale was defined as 1.0 unit of angiogenic activity, and a reading of 1 was considered 0.5 unit; readings of 1 and 2 were the preferred range for quantification. Eyes that demonstrated positive angiogenesis were removed, fixed, and processed for histologic examination to rule out angiogenesis due to the influx of inflammatory cells.

The HPLC fractions were also assayed for mitogenic activity toward capillary endothelial cells by measuring [$^3$H]thymidine incorporation. Mitogenic activity was determined by measuring the incorporation of [$^3$H]thymidine over 24 hr by confluent, serum-starved target cells according to the method of Gospodarowicz, (1075) J. Biol. Chem. 250, 2515–2520. The target cells used in this assay were primary rabbit brain capillary endothelial cells that were isolated and maintained according to the procedure of Bowman et al., (1981) In Vitro 17, 353–362. Routinely, 100 μl of test material plus 0.5 μCi of [$^3$H]thymidine (specific activity, 11 Ci/mmol) was diluted to 1 ml in culture medium. The entire dilution was then used to replace the medium in which $10^5$ confluent, serum-starved capillary endothelial cells were maintained. Data are expressed as a mitogenic index ([$^3$H]thymidine incorporation, experimental/control). The change in the number of capillary endothelial cells incubated with test material was also monitored. The results shown in Table 3 below indicate that the fractions neither had significant mitogenic activity (index ≧ 2.0) when compared to whole wound fluid (index = 26.9), nor increased endothelial cell number. Therefore, most of the mitogenic activity remained in the >$M_r$ 14,000 retentate after acid dialysis of the wound fluid. These data show that wound fluid angiogenesis factor is not a mitogen (index of the angiogenic fraction 5 was 1.03).

Because angiogenesis in vivo requires the migration of capillary endothelial cells toward the angiogenic stimulus, all of the fractions were tested for their ability to stimulate directed migration of capillary endothelial cells through a 10-μm-pore-diameter polycarbonate filter. The potential of purified material to stimulate the directed migration of rabbit brain capillary endothelial cells was determined by a modified migration assay previously used for fibroblasts. See Seppa et al. (1982) J. Cell Biol. 92, 584–588 and Postlewaith et al. (1976) J. Exp. Med. 144, 1188–1203. Solutions to be tested were diluted 10-fold to a final volume of 300 μl in Dulbecco's modified Eagle's medium supplemented with 10% platelet-poor rabbit plasma serum and placed in the bottom of Boyden blind-well chambers. Gelatin-coated 10-μm-pore-diameter polycarbonate filters (Nucleopore, Pleasanton, CA) were placed over the test solution and $2.5 \times 10^4$ capillary endothelial cells suspended in Dulbecco's modified Eagle's medium plus 10% platelet-poor plasma serum were added to the top compartment. Chambers were incubated for 7 hr at 37° C. At the end of the incubation, the tops of the filters were wiped clean. The filters were then fixed, stained, and evaluated by counting the number of cells that had migrated to the bottom side of the filter.

Whole wound fluid and the acid dialysate stimulated capillary endothelial cell migration, as indicated by the results in Table 3 below. The migratory activity of the acid dialysate was recovered in the angiogenic fraction 5, and to a 3-fold lesser extent in fraction 6. Therefore, only angiogenic fraction 5 at 735 ng/ml stimulated migration of capillary endothelial cells. The concentration that maximally stimulated migration was 7.4 ng/ml.

The chromatograph from the HPLC column is shown in FIG. 1. Each of the fractions was assayed for angiogenic activity, mitogenic activity, and for ability to stimulate direct migration of capillary endothelial cells.

The angiogenic activity was found only in fraction 5 as shown below in Table 3.

TABLE 3

| BIOLOGIC ACTIVITY OF CHROMATOGRAPHIC FRACTIONS OF RABBIT WOUND FLUID | | | | |
|---|---|---|---|---|
| Fraction No. | Start of Fraction (min) | Mitogenic index* | Angiogenesis (units/ml) | Migration** (cells/filter) |
| 1 | 5.79 | 0.4 | 0 | 7 |
| 2 | 7.64 | 0.7 | 0 | 8 |
| 3 | 8.43 | 1.55 | 0 | 7 |
| 4 | 9.21 | 1.06 | 0 | 6 |
| 5 | 9.71 | 1.03 | 50 | 128 |
| 6 | 10.66 | 1.15 | 0 | 45 |
| 7 | 11.69 | 1.70 | 0 | 33 |
| 8 | 14.55 | 0.62 | 0 | 11 |

*[$^3$H]thymidine incorporation; experimental/control = index. Index of whole wound fluid = 26.9. Assay volume was 100 μl.
**Area = 12.6 mm$^2$.

A corneal implant containing 150 ng of material from fraction 5 had a 1.0 unit of angiogenic activity. By histologic examination, the angiogenesis due to the material in fraction 5 was not the result of the infiltration of inflammatory cells.

Fraction 5 was purified 9,600-fold by preparative chromatography with a recovery of 81%. Angiogenic activity and protein content of the purified material are shown in Table 4.

TABLE 4

| | | PURIFICATION OF ANGIOGENESIS FACTOR FROM RABBIT WOUND FLUID | | | | |
|---|---|---|---|---|---|---|
| Stage | Volume (ml) | Total angiogenesis (units) | Total protein (mg) | Specific activity (units/mg) | Purification (-fold) | Recovery (%) |
| Wound fluid | 67 | 1,675 | 2,379 | 0.7 | 1 | 100 |
| Acid dialysate 1.8 | ** | 13 | — | — | — | |

TABLE 4-continued
PURIFICATION OF ANGIOGENESIS FACTOR FROM RABBIT WOUND FLUID

| Stage | Volume (ml) | Total angiogenesis (units) | Total protein (mg) | Specific activity (units/mg) | Purification (-fold) | Recovery (%) |
|---|---|---|---|---|---|---|
| Fraction 5 | 27 | 1,350 | 0.2 | 6,750 | 9,643 | 81 |

*$A_{280}$ absorbing material.
**The activity of the concentrated acid dialysate was not quantitatively determined, but it gave a maximal, nonlinear response in the corneal implant assay.

When fraction 5 was rechromatographed it ran true to its original retention time of 10.0 min, as shown by FIG. 2.

The chromatography was monitored at 206 nm, 260 nm, and 280 nm to establish optimal fractionation time. At these wave lengths the angiogenic peak fraction absorbed maximally at 206 nm and minimally at 260 nm. When the rechromatography of the angiogenic fraction was interrupted with the 10.0 min peak in the detector window and scanned from 190 nm to 540 nm, the resulting absorbance spectrum (FIG. 3) had a maximum at 206 nm and a prominent peak at 276 nm without a peak or shoulder at 260 nm. These data are consistent with the interpretation that the angiogenic peak has the absorbance spectrum of a polypeptide or protein.

As estimated by pore-limit dialysis, the molecular size range of wound fluid angiogenesis factor ($M_r$ 2,000–$M_r$ 14,000) is smaller than the $M_r$ 50,000–$M_r$ 100,000 of retinal angiogenesis factor described by D'Amore et al (1981) PNAS USA, 78, 3068–3072, but an order of magnitude larger than the $M_r$ 200–$M_r$ 800 assigned to rumen angiogenesis factor described by Weiss et al. (1979) Br. J. Cancer, 40, 493–496 and Fenselau et al. (1981) J. Biol. Chem. 256, 9605–9611.

What is claimed:

1. A method for isolating a nonmitogenic angiogenesis factor from rabbit wound fluid accumulated at the site of damaged tissue during the process of healing comprising the steps of
    (a) clarifying said fluid by centrifugation;
    (b) dialyzing the clarified fluid from step (a) with acetic acid at about 4° C.;
    (c) removing insoluble material from the retentate from step (b) by centrifugation;
    (d) dialyzing the clarified retentate from step (c) with water at about 4° C.;
    (e) lyophilizing the dialysate from step (d);
    (f) dissolving the product from step (e) in acetic acid;
    (g) fractionating the solution from step (f) by size exclusion chromatography; and
    (h) identifying a fraction from step (g) which exhibits angiogenic activity.

2. The method according to claim 1 wherein said step (b) is conducted in a $M_r$ 2,000 limit dialysis bag with 0.1N acetic acid.

3. The method according to claim 1 wherein said step (d) is conducted in a $M_r$ 14,000 limit dialysis bag with water.

4. The method according to claim 1 wherein said step (g) is performed by high pressure liquid chromatography.

5. The method according to claim 1 wherein said step (h) is conducted by corneal implant assay.

6. The product comprising nonmitogenic angiogenesis factor produced according to the method of claims 1, 2, 3, 4 or 5.

* * * * *

UNITED STATES PATENT AND TRADEMARK OFFICE
CERTIFICATE OF CORRECTION

PATENT NO. : 4,503,038

DATED : March 5, 1985

INVENTOR(S) : Michael J. Banda, et al.

It is certified that error appears in the above—identified patent and that said Letters Patent is hereby corrected as shown below:

In Table 4, at the base of column 4, the line beginning with the words "Acid dialysate" should read as follows:

Acid dialysate   1.8   **   13   -   -   -

Signed and Sealed this

Twenty-second Day of October 1985

[SEAL]

Attest:

Attesting Officer

DONALD J. QUIGG

Commissioner of Patents and Trademarks—Designate